United States Patent [19]

Urdea et al.

[11] Patent Number: 4,910,300
[45] Date of Patent: Mar. 20, 1990

[54] METHOD FOR MAKING NUCLEIC ACID PROBES

[75] Inventors: Michael S. Urdea, Alamo; Thomas Horn, Berkeley, both of Calif.

[73] Assignee: Chiron Corporation, Emeryville, Calif.

[21] Appl. No.: 190,698

[22] Filed: May 5, 1988

Related U.S. Application Data

[60] Division of Ser. No. 945,876, Dec. 23, 1986, which is a continuation-in-part of Ser. No. 807,624, Dec. 11, 1985.

[51] Int. Cl.$^4$ .................... C07H 19/00; C07H 21/00
[52] U.S. Cl. .................................. 536/287; 536/24; 536/26; 536/27; 435/6
[58] Field of Search .................. 536/24, 27, 28; 435/6

[56] References Cited

FOREIGN PATENT DOCUMENTS

| | | |
|---|---|---|
| 0063879 | 11/1982 | European Pat. Off. |
| 123300 | 10/1984 | European Pat. Off. |
| 8301459 | 4/1983 | PCT Int'l Appl. |
| 8403285 | 8/1984 | PCT Int'l Appl. |
| 2156074 | 10/1985 | United Kingdom |
| 2169403 | 7/1986 | United Kingdom |

OTHER PUBLICATIONS

Reeves et al–Biochemistry vol. 24(1985) pp. 2262–2268.
Leary et al., *Proc. Natl. Acad. Sci.* USA (1983) 80:4045–4049.
McBride et al., *Tet. Lett.* (1983) 24(3):245–248.
Meinkoth et al., *Anal. Biochem.* (1984) 138:267–284.
Ranki et al., "Nucleic Acid Sandwich Hybridization in Adenovirus Diagnosis" New Developments in Diagnostic Virology, New York, Springler-Verlag (1983).
Ranki et al., *Gene* (1983) 21:77–85.
Renz et al., *Nuc. Acids. Res.* (1984) 92(8):3435–3444.
Richardson et al., *Nuc. Acids Res.* (1983) 11 (8):6167–6184.
Sanchez-Pescador et al., *DNA* (1984) 3(4):339–343.
Smith et al., *Nuc. Acids. Res.* (1985) 13(7):2399–2412.
Syvanen et al., *Nuc. Acids. Res.* (1986) 14(12):5037–5047.
Valenzuela et al., "The Nucleotide Sequence of the Hepatitis B. Viral Genome and the Identification of the Major Viral Genes" Animal Virus Genetics, NY, Acad. Press, 1980.
Virtanen et al., *The Lancet* (Feb. 19, 1983) pp. 381–383.
Warner et al., *DNA* (1984) 3(5):401–411.
Draper *Nucl. Acids. Res.* 1984) 12(2):989–1002.
Sung *J. Org. Chem.* (1982) 47:3623–3628.
Sung *Nucl. Acids Res.* (1981) 9(22):6139–6151.
Gillam et al., *Anal. Biochem.* (1986) 157:199–207.

*Primary Examiner*—Sam Rosen
*Attorney, Agent, or Firm*—Irell & Manella

[57] ABSTRACT

Modified nucleotides are provided which have the structure

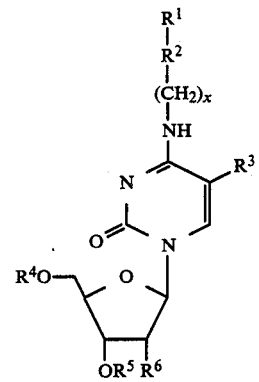

wherein $R^1$ is a reactive group derivatizabale with a detectable label, $R^2$ is an optional linking moiety including an amide, thioether or disulfide linkage or a combination thereof. $R^3$ is hydrogen, methyl, bromine, fluorine or iodine, $R^4$ is hydrogen, an acid-sensitive, base-stable blocking group or an acyl capping group, $R^5$ is hydrogen or a phosphorus derivative, $R^6$ is H, OH, or OR where R is a protecting group and x is an integer in the range of 1 and 8 inclusive. Methods of synthesizing the derivatizable nucleotide are disclosed, as are labeled polynucleotide probes prepared therefrom.

6 Claims, No Drawings

METHOD FOR MAKING NUCLEIC ACID PROBES

CROSS-REFERENCE TO RELATED APPLICATIONS

This application is a division of application Ser. No. 945,876 filed Dec. 23, 1986 which is a continuation-in-part of U.S. Ser. No. 807,624 filed Dec. 11, 1985.

FIELD OF THE INVENTION

This invention relates generally to polynucleotide probes, and in particular relates to a polynucleotide probe containing at least one labeled, modified nucleotide.

DESCRIPTION OF RELEVANT LITERATURE

Meinkoth and Wahl, *Anal. Biochem.*, (1984) 138:267–284, provide a review article of hybridization techniques. See also Leary et al., *Proc. Natl. Acad. Sci. USA* (1983) 80:4045–4049, for a description of the dot blot assay. Sandwich hybridization is described by Ranki et al., *Curr. Top. Microbiol. Immunology* (1983) pp. 308ff. See also Ranki et al., *Gene* (1983) 21:77–85, Virtanen et al., *Lancet* (1983) 381–383, and U.S. Pat. No. 4,486,539. European Pat. No. 123,300 describes biotin-avidin complexes for use in detecting nucleic acid sequences. Sung, in *Nucl. Acids Res.* 9(22):6139–6151 (1981) and in *J. Org. Chem.* 47:3623–3628 (1982), discusses the synthesis of a modified nucleotide and application of the modified structure in oligonucleotide synthesis. Modified nucleotides are also discussed in Draper, *Nucleic Acids Res.* 12:2:989–1002 (1984), wherein it is suggested that cytidine residues in RNA be modified so as to bind to reporter molecules. Later work suggests similar modification of cytidine residues in DNA (*Anal. Biochem.* 157(2):199 (1986). European patent application Ser. No. 063879, filed 6 Apr. 1982, and PCT application No. PCT/US84/00279 also describe modified nucleotides and applications thereof.

BACKGROUND OF THE INVENTION

The increasing ease of cloning and synthesizing DNA sequences has greatly expanded opportunities for detecting particular nucleic acid sequences of interest. No longer must one rely on the use of immunocomplexes for the detection of pathogens, ligands, antigens, and the like. Rather than detecting particular determinant sites, one can detect DNA sequences or RNA sequences associated with a particular cell. In this manner, diseases can be diagnosed, phenotypes and genotypes can be analyzed, as can polymorphisms, relationships between cells, and the like.

Analyses of DNA sequences typically involve the binding of an analyte sequence to a solid support and hybridization of a complementary sequence to the bound sequence. The annealing and complexing steps usually involve an extended period of time and require careful washing to minimize non-specific background signals. Applicants' co-pending application Ser. No. 807,624, describes new techniques for analyzing nucleic acid sequences which are faster, minimize the number of manipulative steps, and provide for an increased signal to noise ratio. This application, a continuation-in-part of Ser. No. 807,624, the disclosure of which is incorporated by reference herein, is directed in particular to novel polynucleotide probes useful, inter alia, in the techniques described in applicants' co-pending parent application.

The majority of polynucleotide probes in current use are radioactively labeled, e.g. with isotopes of hydrogen ($^3$H), phosphorus ($^{32}$P), carbon ($^{14}$C) or iodine ($^{125}$I). These materials are relatively simple to synthesize by direct inclusion of the radioactive moieties, e.g. by kinasing with $^{32}$P-labeled ATP, equilibrating with tritiated water, or the like. As is well known, however, use of such radioactive labels has drawbacks, and other detectable species which are not radioactive are preferred.

In order to incorporate other, non-radioactive types of detectable species in a nucleotide, some sort of chemical modification of the nucleotide is required. It is widely recognized that nucleotide modification is a difficult and sensitive procedure, as any modification reaction has to be mild enough to leave the RNA or DNA molecules intact, while giving a modified nucleotide product which can participate in normal base pairing and stacking interactions. These considerations typically limit nucleotide substitution positions to the 5-position of a pyrimidine and the 8-position of a purine, as noted in the literature (see, e.g., European patent application Ser. No. 063879, cited supra).

Other considerations must also be taken into account. Base pairing may be hindered during hybridization if the detectable label is at one end of the nucleotide chain rather than present at some point within it. Further, it has proved difficult to provide even non-radioactively labeled probes which may be inexpensively synthesized in large quantity. Thus, many known probes are limited in their potential applications.

SUMMARY OF THE INVENTION

Accordingly, it is an object of the present invention to overcome the aforementioned disadvantages of the prior art.

It is another object of the present invention to provide a novel modified nucleotide useful in the synthesis of labeled polynucleotide probes.

It is still another object of the present invention to provide a nucleotide modified at the 4-position of a pyrimidine base so as to include an alkylamine or other reactive moiety which is derivatizable with a detectable label.

It is yet another object of the present invention to provide a nucleotide so modified at the 4-position which is further modified at the 5-position.

It is a further object of the present invention to provide a labeled polynucleotide probe, at least one pyrimidine nucleotide of which is modified at the 4-position so as to be derivatizable with a detectable label.

It is still a further object of the invention to provide methods of making derivatizable alkylamine nucleotides.

It is another object of the invention to provide a method of using a probe labeled according to the method of the present invention to detect the presence of known nucleic acid sequences in a sample.

Additional objects, advantages and novel features of the invention will be set forth in part in the description which follows, and in part will become apparent to those skilled in the art of examination of the following, or may be learned by practice of the invention.

In one aspect of the invention, a modified, derivatizable nucleotide is provided having the structure of Formula 1:

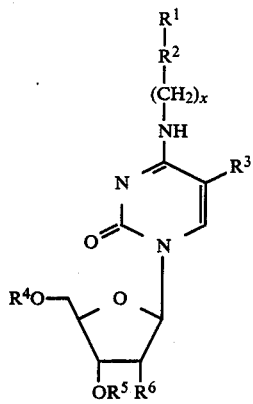

Formula 1 wherein $R^1$ is a reactive group derivatizable with a detectable label, which reactive group may be amine, carboxyl or thiol and further may be protected for various synthetic manipulations, $R^2$ is an optional linking moiety such as those typically used to label proteins, and includes an amide, thioether or disulfide linkage or a combination thereof, $R^3$ is selected from the group consisting of hydrogen, methyl, bromine, fluorine and iodine, $R^4$ is hydrogen, an anchoring group which covalently binds the structure to a solid support, or a blocking group such as dimethoxytrityl or pixyl, which blocking group is generally base-stable and acid-sensitive, $R^5$ is hydrogen, an anchoring group which covalently binds the structure to a solid support, or a phosphorus derivative enabling addition of nucleotides at the 3' position, and may be, for example, $PO_3H_2$, a phosphotriester, a phosphodiester, a phosphite, a phosphoramidite, H-phosphonate or a phosphorothioate, and $R^6$ is H, OH, or OR where R is a functional group useful as a protecting moiety in RNA synthesis, and x is an integer in the range of 1 and 8 inclusive.

In another aspect of the invention, a method of making the above modified nucleotide is provided including the step of derivatizing the $R^1$ moiety with a detectable label.

In still another aspect, a polynucleotide probes is provided using one or more of the above modified nucleotides. The probe can be used to screen a sample containing a plurality of single-stranded or double-stranded polynucleotide chains, and will label the desired sequence, if present, by hybridization.

DETAILED DESCRIPTION OF THE INVENTION

"Derivatizable" nucleotides are nucleotides modified so as to include at the 4-position of a pyrimidine a functional group which can react with a detectable label. An example of a derivatizable nucleotide is one which has been modified at the 4-position with an alkylamine moiety so that a free amine group is present on the structure.

"Derivatized" nucleotides are nucleotides in which the derivatizable functional group at the 4-position of the pyrimidine is bound, covalently or otherwise, directly or indirectly, to a detectable label.

"Alkylamine nucleotides" are nucleotides having an alkylamine group at the 4-position of a pyrimidine, bound to the stucture in such a way as to provide a free amine group at that position.

A "polynucleotide" is a nucleotide chain structure containing at least two nucleotides. The "polynucleotide probe" provided herein is a nucleotide chain structure, as above, containing at least two nucleotides, at least one of which includes a modified nucleotide which has substantially the same structure as that given by Formula 1.

"Detectable label" refers to a moiety which accounts for the detectablility of a complex or reagent. In general, the most common types of labels are fluorophores, chromophores, radioactive isotopes, and enzymes.

"Fluorophore" refers to a substance or portion thereof which is capable of exhibiting fluorescence in the detectable range. Typically, this fluorescence is in the visible region, and there are common techniques for its quantitation. Examples of fluorophores which are commonly used include fluorescein (usually supplied as fluorescein isothiocyanate [FITC] or fluorescein amine), rhodamine, dansyl and umbelliferone.

The nucleotide numbering scheme used herein is illustrated by Formulae 2-5.

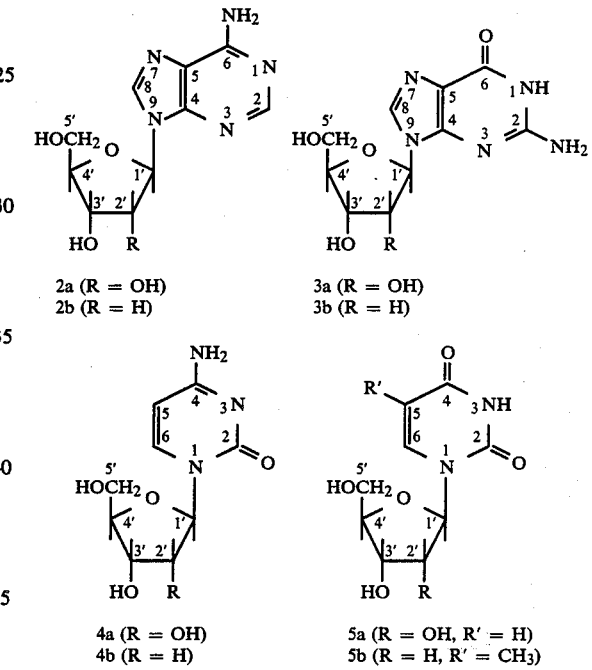

2a (R = OH)
2b (R = H)

3a (R = OH)
3b (R = H)

4a (R = OH)
4b (R = H)

5a (R = OH, R' = H)
5b (R = H, R' = CH₃)

In a preferred embodiment, the substituents of the modified nucleotide of Formula 1 are as follows.

$R^1$, which is a reactive group derivatizable with a detectable label, is preferbly $-NH_2$, $-COOH$ or $-SH$.

$R^2$ is an optional linker moiety which contains an amide, thioether or disulfide linkage, or a combination thereof. $R^2$ is preferably a heterobifunctional linker such as those typically used to bind proteins to labels. In most cases, a free amino group on a protein or other structure will react with a carboxylic acid or activated ester moiety of the unbound $R^2$ compound so as to bind the linker via an amide linkage. Other methods of binding the linker to the nucleotide are also possible. Examples of particularly preferred linkers include.

Formula 6

-continued

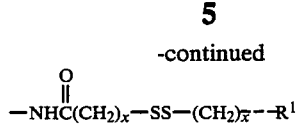

Formula 7

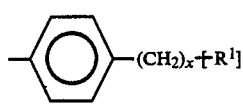

Formula 8 wherein x is an integer in the range of 1 and 8 inclusive.

As many be seen in Formula 1, the linker, if present, is attached to the nucleotide structure through an alkylamine functionality —NH—$(CH_2)_x$— wherein x is an integer in the range of 1 and 8 inclusive, and the alkylamine functionality is present at the 4-position of the pyrimidine base.

As noted above, $R^3$ is hydrogen, methyl, bromine, fluorine or iodine. Thus, the base of the nucleotide is a pyrimidine optionally substituted at the 5-position with the aforementioned $R^3$ substituents.

$R^4$ is typically hydrogen, if the modified nucleotide is a terminal 5' structure, or a suitable blocking group useful in polynucleotide synthesis. Examples of suitable blocking groups include substituted and unsubstituted aralkyl compounds, where the aryl is, e.g., phenyl, naphthyl, furanyl, biphenyl and the like, and where the substituents are from 0 to 3, ususally 0 to 2, and include any non-interfering stable groups, neutral or polar, electron-donating or withdrawing, generally being of 1 to 10, usually 1 to 6 atoms and generally of from 0 to 7 carbon atoms, and may be an aliphatic, alicyclic, aromatic or heterocyclic group, generally aliphatically saturated, halohydrocarbon, e.g., trifluoromethyl, halo, thioether, oxyether, ester, amide, nitro, cyano, sulfone, amino, azo, etc.

In one or more steps during nucleotide chain synthesis, it may be desirable to replace the hydrogen atom or blocking group at the $R^4$ position with a more stable, "capping" group. Suitable capping groups include acyl groups which provide for stable esters. The acyl groups may be organic or inorganic, including carboxyl, phosphoryl, pyrophosphoryl, and the like. Of particular interest are alkanoic acids, more particularly aryl-substituted alkanoic acids, where the acid is at least 4 carbon atoms and not more than about 12 carbon atoms, usually not more than about 10 carbon atoms, with the aryl, usually phenyl, substituted alkanoic acids usually of from 8 to 12 carbon atoms. Various heteroatoms may be present such as oxygen (oxy), halogen, nitrogen, e.g., cyano, etc. For the most part the carboxylic acid esters will be base labile, while mild acid stable, particularly at moderate temperatures below about 50° C., more particularly, below about 35° C. and at pHs greater than about 2, more particularly greater than about 4.

The modified nucleotide may also be attached to a support through the $R^4$ position so as to facilitate addition of labeled or unlabeled nucleotides at the 3' ($R^5$) position. In such a case, $R^4$ is an anchoring group as will be described below. Covalent attachment to a support is also preferred during sample screening, as the time and complexity of separating the hybridized nucleotide chains from the sample is substantially reduced. When the modified nucleotide of Formula 1 is bound to one or more additional nucleotides at the 5' position, the $R^4$ substituent is replaced with such additional nucleotides which are bound through their 3' phosphate groups.

$R^5$, as noted, is hydrogen or a phosphorus derivative such as $PO_3H_2$, a phosphotriester, a phosphodiester, a phosphite, a phosphoramidite, an H-phosphonate or a phosphorothioate suitable for polynucleotide synthesis, which derivative enables sequential addition of nucleotides at the 3' position. More generally, such phosphorus derivatives are given by Formula 9 and Formula 10:

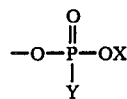 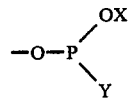

Formula 9   Formula 10 wherein X is preferably hydrogen or an aliphatic group, particularly a saturated aliphatic group, a β-heterosubstituted aliphatic group, where the β-substituent is an electron-withdrawing group which readily participates in β-elimination, either as the leaving group or the proton-activating group, substituted methylene, where the substituent may vary widely and supports a negative charge on the methylene through inductive or resonating effects; aryl; and aralkyl. Depending on the nature of the phosphorus functionality, one group may be chosen over another. Thus, depending upon whether a phorphorchloridite, phosphoramidite, phosphate, thiophosphate, phosphite, or the like, is employed, particular phosphoro ester groups will be preferred.

Similarly, the groups employed for Y will depend upon the nature of the phosphorus derivative employed for oligomerization. When the phosphoramidite is employed, Y will have the formula —$NT^1T^2$, where $T^1$ and $T^2$ may be the same or different and may be hydrocarbon or have from 0 to 5, usually 0 to 4 heteroatoms, primarily oxygen as oxy, sulfur as thio, or nitrogen as amino, particular tert.-amino, $NO_2$ or cyano. The two T's may be taken together to form a mono- or polyheterocyclic ring having a total of from 1 to 3, usually 1 to 2 heteroannular members and from 1 to 3 rings. Usually, the two T's will have a total of from 2 to 20, more usually 2 to 16 carbon atoms, where the T's may be aliphatic (including alicyclic), particularly saturated aliphatic, monovalent, or, when taken together, divalent radicals, defining substituted or unsubstituted heterocyclic rings. The amines include a wide variety of saturated secondary amines such as dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine and similar saturated monocyclic nitrogen heterocycles.

$R^5$ may also represent a point of attachment for one or more additional nucleotides at the 3' position. In that case $R^5$ is phosphate, as such additional nucleotides are typically bound through a phosphate group.

As at the 5' position, the modified nucleotide may be attached to a support through the 3' position, i.e. through $R^5$. When the nucleotide thus attached to a support, $R^5$ is an anchoring group as will be described below.

$R^6$, in the case of deoxyribose, is H; in the case of ribose, is OH;, and, during RNA synthesis, is a suitable blocking group which protects the —OH moiety from modification. Blocking groups useful here generally include those given above for $R^4$, and the specific choice of blocking group will be apparent to one skilled in the art. Examples of blocking groups which are preferred at the $R^6$ position during RNA synthesis include silyl ethers such as t-butyldimethylsilyl, substituted methyl ethers, o-nitrobenzyl ether, esters such as levulinic ester, and the following pyranyl structures given by Formula 11 (tetrahydropyranyl) and Formula 12 (4-methoxytetrahydropyranyl):

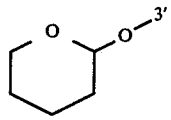

Formula 11

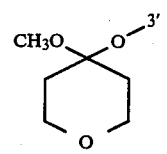

Formula 12

A particularly preferred blocking group is orthonitrobenzyl. Additional examples of suitable blocking groups may be found in Green, T.W., *Protective Groups in Organic Synthesis*, New York: Wiley & Sons, 1981.

The modified nucleotide will normally be derivatized with a label in a manner which will allow for detection of complex formation. A wide variety of labels may be used, and one or another label may be selected depending upon the desired sensitivity, the equipment available for measuring, the particular protocols employed, ease of synthesis, and the like. Labels which have found use include enzymes, fluorescers, chemiluminescers, radionuclides, enzyme substrates, cofactors or suicide inhibitors, specific binding pair members, particularly haptens, or the like. The molecule involved with detection may be covalently bound to the modified nucleotide or indirectly bound through the intermediacy of a specific binding pair, i.e. ligand and receptor. Examples of ligands and receptors include biotin-avidin, hapten-antibody, ligand-surface membrane receptor, metal-chelate, etc.

As suggested above, it is preferred that the modified nucleotide be covalently bound to a support of either the $R^4$ or $R^5$ positions for oligonucleotide synthesis. A wide variety of supports may be used, including silica, Porasil C, polystyrene, controlled pore glass (CPG), kieselguhr, poly(dimethylacrylamide), poly(acrylmorpholide), polystyrene grafted onto poly(tetrafluoroethylene), cellulose, Sephadex LH-20, Fractosil 500, etc.

Depending on the nature of the support, different functionalities will serve as anchors. As noted above, these "anchoring" groups are at either the 3' or the 5' position, i.e. at either the $R^5$ or $R^4$ positions, respectively. For silicon-containing supports, such as silica and glass, substituted alkyl or aryl silyl compounds will be employed to form a siloxane or siloximine linkage. With organic polymers, ethers, esters, amines, amides, sulfides, sulfones and phosphates may find use. For aryl groups, such as polystyrene, halomethylation can be used for functionalization, where the halo group may then be substituted by oxy, thio (which may be oxidized to sulfone), amino, phospho (as phosphine, phosphite or phosphate), silyl or the like. With a diatomaceous earth element (e.g., kieselguhr), activation may be effected by a polyacrylic acid derivative and the active functionality reacted with amino groups to form amine bonds.

Polysaccharides may be functionalized with inorganic esters, e.g. phosphate, where the other oxygen serves to link the chain. With polyacrylic acid derivatives, the carboxyl or side chain functionality, e,g., N-hydroxyethyl acrylamide, may be used in conventional ways for joining the linking group.

The modified nucleotide of Formula 1, as previously suggested, can be used as a substrate for synthesis of polynucleotide probes. Additional nucleotides may be sequentially added at the 5' position by, for example, the phosphoramidite method of Beaucage and Caruthers, *Tetrahedron Lett.* 22(20):1859-62 (1981) or the phosphotriester method of Itakura, *J. Biol. Chem.* 250:4592 (1975), or the like, or at the 3' position by the method of Belagaje and Brush, *Nuc. Acids Research* 10:6295 (1982), or both. The nucleotrides which are sequentially added may be unlabeled, or they may be modified according to Formula 1 and derivatized with a label at the $R^1$ moiety. Accordingly, one or more labels may be present within a polynucleotide chain rather than at one end.

This polynucleotide probe includes at least one modified nucleotide having substantially the same structure as that given by Formula 1, i.e. including at least one modified nucleotide having the structure given by Formula 13:

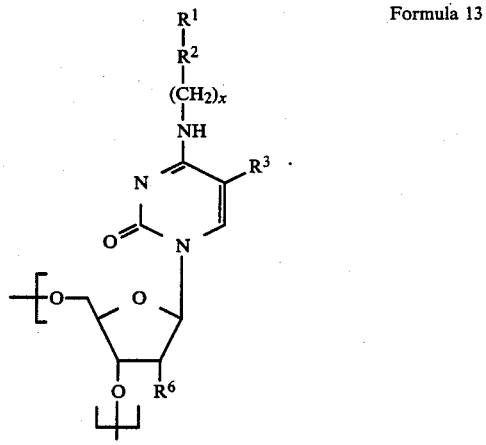

Formula 13 wherein $R^1$ is a reactive group derivatized with a detectable label, $R^2$ is an optional linking moiety including an amide, thioether or disulfide linkage or a combination thereof, $R^3$ is selected from the group consisting of hydrogen, methyl, bromine, fluorine and iodine, $R^6$ is H, OH, or OR where R is an acid-sensitive, base-stable protecting group and x is an integer in the range of 1 and 8 inclusive. The polynucleotide probe may have a single label of a plurality of labels, depending upon the nature of the label and the mechanism for detection. Where the label is fluorescent, for example, a distance of at least 3 to 12 Angstroms should be maintained between fluorescent species to avoid any fluorescence quenching.

Such labeled polynucleotide probes may be used in the assays described in applicants' co-pending application Ser. No. 807,624, or in any number of other applications, includiing conjugation with enzymes, antibodies and solid supports. An example of one such use of applicants' novel oligonucleotide probes is in the detection of a known sequence of DNA. The probe may be prepared so as to be attached, for example, to a standard latex solid support or to an avidin support in the case of biotin-labeled probes. Sample containing single-stranded or double-stranded DNA sequences to be analyzed is caused to contact the probe for a time sufficient for hybridized nucleic acid complexes to form, and any such complexes are detected by means of the fluorescent, biotin or otherwise detectable label.

Synthesis of the modified nucleotide: The present invention also relates to a method of synthesizing the novel modified nucleotide of Formula 1. In the preferred embodiment, a pyrimidine nucleotide is provided which has the structure of Formula 14 or Formula 15:

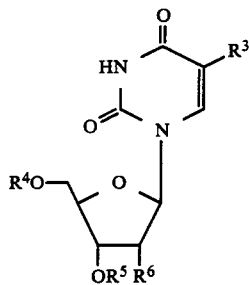 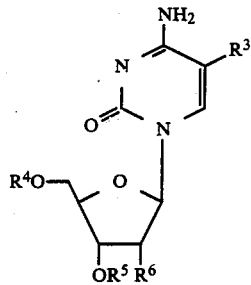

Formula 14   Formula 15 wherein $R^3$ is as given above, $R^4$ and $R^5$ are hydrogen, and $R^6$ is OH or H. The 5' position of the sugar ring—and the 2' position as well if the sugar is ribose rather than deoxyribose—is then protected against modification during subsequent reaction steps by addition of a dimethoxytrityl group (see Example 3) or other suitable protecting group, the addition reaction allowed to proceed for a time sufficient to ensure substantial completeness. Similarly, the 3' hydroxyl group is protected with a silyl or other suitable functionality (see Example 4).

Examples of particularly suitable protecting groups include those set forth above as "$R^6$", i.e., substituted methyl ethers, esters, pyranyls and the like.

When the nucleoside is thymine or uracil, or uracil modified at the 5-position by an $R^3$ substituent, i.e. a pyrimidine or substituted pyrimidine which has an oxy rather than an amino substituent at the 4-position, the carbonyl is converted to an amine moiety by, for example, reaction with an activating agent such as 1-(mesitylene-2-sulfonyl)-tetrazole (MS-tet) or other suitable condensing reagent. Activating agents for use herein also include other sulfonyl compounds given by the formula $E_1$—$SO_2$—$E_2$ wherein $E_1$ is tetrazoyl, nitrotriazoyl, triazoyl, imidazoyl, nitroimidazoyl, or the like, and $E_2$ is an aryl or substituted aryl group such as mesitylene, etc. Another class of suitable activating agents is given by Formula 16:

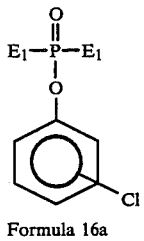 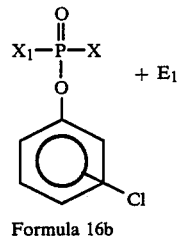

Formula 16a   Formula 16b wherein $E_1$ is as defined above. In Formula 16b, $E_1$ is present in a solution containing the activating agent but is not bound thereto, and X is a halogen substituent, preferably chlorine. In general, any activating agent may be used and may include one or more halogen substituents, preferably chlorine, on the ring structure which after reaction can be displaced by ethylene diamine or like reagent. This conversion is followed by reaction with an alkyldiamine such as ethylenediamine to give a nucleotide having a —NH—$(CH_2)_x$NH$_2$ functionality at the 4-position of the pyrimidine ring (see Examples 5, 6). The free amine group so provided is then optionally reacted with caproic acid, an actiivated caproic acid ester, or with a caproic acid derivative such as 6-aminocaproic acid, in order to ensure sufficient spacing between the nucleotide and the detectable label to be attached at the $R^1$ moiety. The caproic acid or related compound may be labeled prior to attachment (see Example 7) or subsequently.

When the nucleoside is cytosine or a 5-modified cytosine, i.e. substituted with an $R^3$ other than hydrogen, the exocyclic amino functionality can be converted to an $N^4$-aminoalkyl or $N^4$-aminoaryl cytosine by reaction with an aryl sulfonyl chloride followed by reaction with an alkyl- or aryldiamine (Scheme I). See, e.g., Markiewicz, W. T. and R. Kierzek, 7th Intl. Round Table, pp. 32 and 72 (1986). Alternatively, preparation of $N^4$-substituted cytosine may be effected using a bisulfite-catalyzed exchange reaction. See Schulman, L. H. et al., Nuc. Acids Res. 9:1203-1217 (1981) and Draper, D. E., Nuc. Acids. Res. 12:989-1002 (1984).

Scheme I

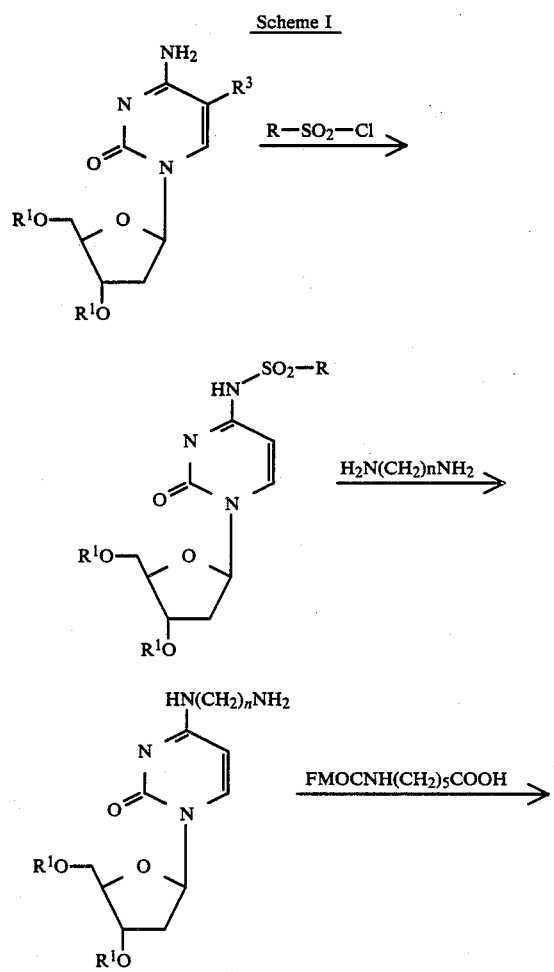

Scheme I
-continued

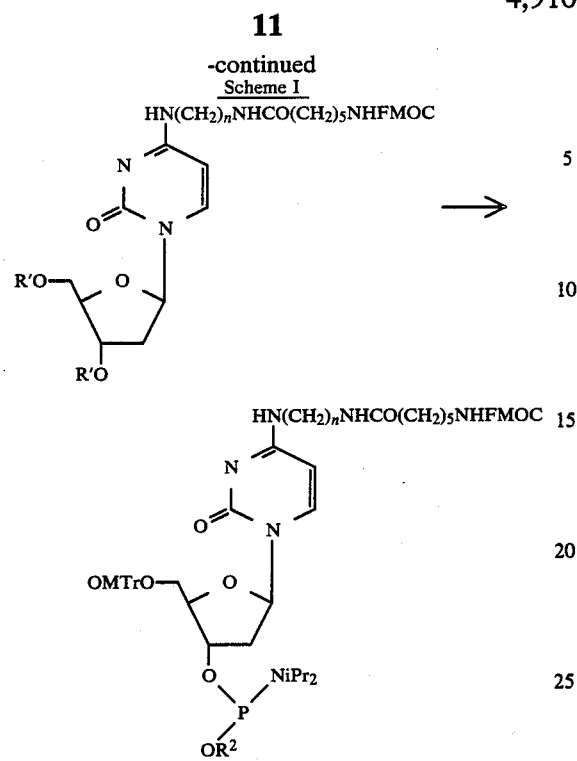

EXAMPLE 2
6-N⁴-(2-Aminoethyl)-Deoxycytidine

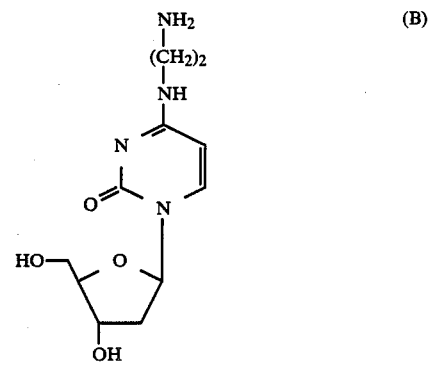

An alkylated derivative of deoxycytidine, N⁴-(2-aminoethyl) deoxycytidine (B) was prepared from properly protected deoxyuridine via the 4-tetrazoyl derivative as described by Reese and Ubasawa, *Tetrahedron Lett.* 21:2265 (1984). This latter derivative was converted to B by displacement of the tetrazoyl moiety with ethylene diamine essentially as described by Sung, *J. Org. Chem.* 47:3623 (1982) and Maggio et al., *Tetrahedron Lett.* 25:3195 (1984). The corresponding 5'-DMT-3'-phosphoramidite N⁴-(2-N-trifluoroacetylaminoethyl) deoxycytidine was prepared by blocking the alkylamine with trifluoroacetic anhydride and then preparing the corresponding N,N-diisopropyl phosphoramidite as described (Beaucage and Caruthers, supra; McBride and Caruthers, *Tetrahedron Lett.* 24:245 (1983)).

matography (Warner and Legg, *Inorg. Chem.* 18:1839 (1979)). The dried product was suspended in 10 ml of 1:1 DMF/THF (v/v) to which 1.5 mmole of N-hydroxy succinimide and 1 mmole of dicyclohexylcarbodiimide were added. After 18 h at room temperature the solution was filtered through glass wool and diluted to a 0.2M final concentration of A with DMF (assuming a 100% yield from step 1).

Scheme II

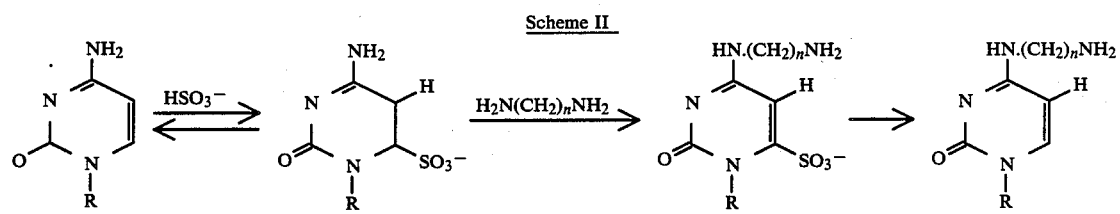

Alternatively, where the alkylamine group is more than about 6 carbon atoms long, the free amine group thereof may directly bond to a suitable detectable label.

The synthesis may further include removal of the dimethoxytrityl or other protecting groups with acid, followed by, if desired, phosphorylation or phosphitylation of the 3' position in preparation for sequential addition of nucleotides.

It is to be understood that while the invention has been described in conjunction with the preferred specific embodiments thereof, that the foregoing description as well as the examples which follow are intended to illustrate and not limit the scope of the invention, which is defined by the scope of the appended claims. Other aspects, advantages and modifications within the scope of the invention will be apparent to those skilled in the art to which the invention pertains.

EXAMPLES

EXAMPLE 1

Labeling of Caproic Acid Derivative

(A)

To 1 mmole of fluorescein isothiocyanate in 5 ml of DMF was added 2 mmole of 6-aminocaproic acid and 540 μl of triethylamine. After 24 h at room temperature, the product was isolated by preparative thin layer chro-

EXAMPLE 3

5'-Dimethoxytrityl-2'-Deoxyuridine

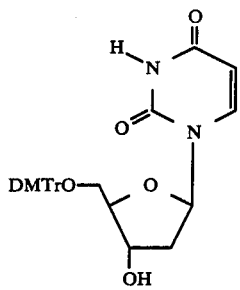
(C)

To 2-Deoxyuridine (10 g, 44 mmole) dried by coevaporation of pyridine and suspended in pyridine (100 ml) was added 18.4 g (54 mmole) 4,4'-dimethoxytrityl chloride (DMT-Cl). The reaction was allowed to proceed for 18 h at room temperature, and 100 ml methanol was added to deactivate excess DMT-Cl. Most of the pyridine was then removed in vacuo, and the residue, dissolved in 500 ml ethyl acetate, was washed with saturated aqueous $NaHCO_3$ (3×500 ml). The organic phase was dried over solid $Na_2SO_4$ and evaporated to dryness. The residue was purified by flash chromatography on silica gel to give 18.0 g (77%) of 5'-dimethoxytrityl-2'-deoxyuridine (C).

EXAMPLE 4

5'-O-(4,4'-Dimethoxytrityl)-3'-t-Butyldimethylsilyl-2'-Deoxyuridine

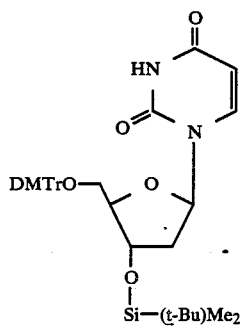
(D)

To 18 g (34 mmole) of C in 200 ml DMF was added imidazole (5.8 g, 85 mmole) with rapid stirring to assure complete dissolution. t-Butyldimethylsilyl chloride (7.65 g, 51 mmole) dissolved in a small volume of DMF was added dropwise with stirring and the reaction was allowed to proceed in the dark for 18 h at room temperature. The reaction mixture was diluted with ethyl acetate (250 ml) and extracted with $NaHCO_3$ (3×250 ml). The organic phase was dried over $Na_2SO_4$ and evaporated to dryness. The residue was purified by flash chromatography on silica gel to give 15.0 g (68% yield) of 5'-O-(4,4'-dimethoxytrityl-3'-t-butyldimethylsilyl-2'-deoxyuridine (D).

EXAMPLE 5

4-(1,2,3,4-Tetrazol-1-yl)-[5'-(4,4'-Dimethoxytrityl)-3'-t-Butyldimethylsilyl-β-D-2'-Deoxyribosyl] Pyridine-2(1H)-one

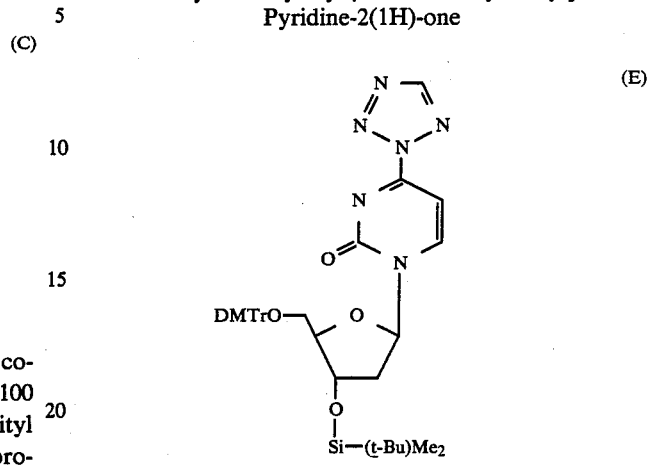
(E)

To 15.0 g (23 mmole) of D, dried by coevaporation of pyridine and dissolved in pyridine (50 ml) was added diphenylphosphate (2.9 g, 11.5 mmole) dissolved in pyridine (5 ml). 1-(Mesitylene-2-sulfonyl)-tetrazole (MS-tet) (15.5 g, 61.5 mmole) dissolved in pyridine (45 ml) was added and the reaction mixture allowed to proceed in the dark for 18 h at room temperature. To the dark brown reaction mixture was added 25 ml water. After 30 min, the product was concentrated under reduced pressure. The residue was dissolved in 250 ml methylene chloride, washed with an aqueous $NaHCO_3$ solution (3×250 ml), dried over $Na_2SO_4$, and the solvent was removed under reduced pressure in the presence of toluene. The residue was purified by flash chromatography on silica gel to give 10.0 g (62%) of 4-(1,2,3,4-Tetrazol-1-yl)-[5'-(4,4'-dimethoxy-trityl)-3'-t-butyldimethylsilyl-β-D-2'-deoxy-ribosyl]-pyridine-2(1H)-one (E).

EXAMPLE 6

4-N-(2-Aminoethyl)-5'-Dimethoxytrityl-3'-t-Butyldimethylsilyl-2'-Deoxycytidine

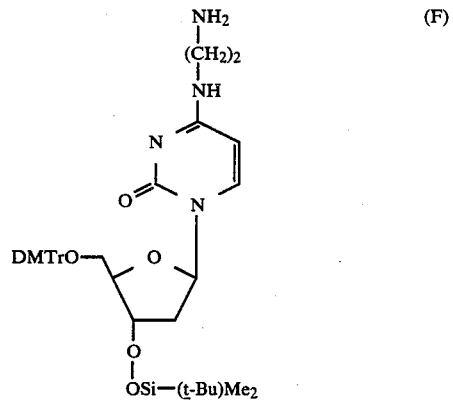
(F)

To a solution of ethylene diamine (9.3 ml, 143 mmole) in dioxane (100 ml) cooled to 5° C. was added E (10.0 g, 14.3 mmole) and left for one hour. The solvent was removed at reduced pressure and the residue was coevaporated with toluene to remove excess ethylene diamine. The product was purified by chromatography on a silica gel column, eluted with 12-20% methanol in methylene chloride to give 7.15 g (75%) of 4-N-(2-aminoethyl)-5'-dimethoxytrityl-3'-t-butyldimethylsilyl-2'-deoxycytidine (F). The product was shown to react positively with ninhydrin, confirming the presence of a free amine moiety.

EXAMPLE 7

N$^4$-(N-FMOC-6-Aminocaproyl-2-Aminoethyl)-5'-Dimethyltrityl-3'-t-Butyldimethylsilyl-2'-Deoxycytidine

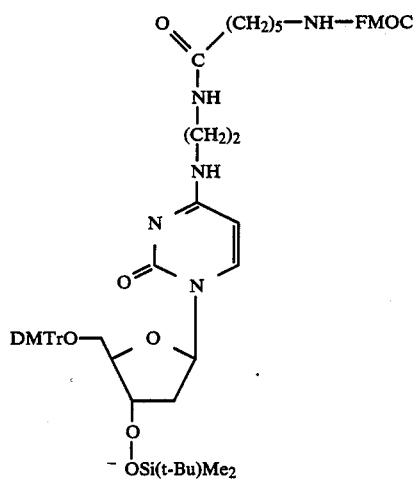

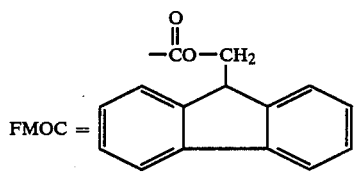

To a solution of F (6.5 g, 9.6 mmole) in pyridine (50 ml) was added N-FMOC-6-aminocaproic acid (4.26 g, 12 mmole) (FMOC represented by structure H) and DCC (2.96 g, 14.4 mmole). After 3 h, the reaction was complete as judged by tlc (silica in 10% methanol/methylene chloride). Pyridine was removed at reduced pressure. The residue was extracted with ethyl acetate, insoluble dicyclohexylurea (DCHU) filtered off and the solvent removed. The product was isolated by silica gel chromatography eluted with 4% methanol in methylene chloride affording 7.3 g (70%) of N$^4$-(N-FMOC-6-amino-caproyl-2-amino-ethyl)-5'-dimethyltrityl-3'-t-butyldi-methylsilyl-2'-deoxycytidine (G).

EXAMPLE 8

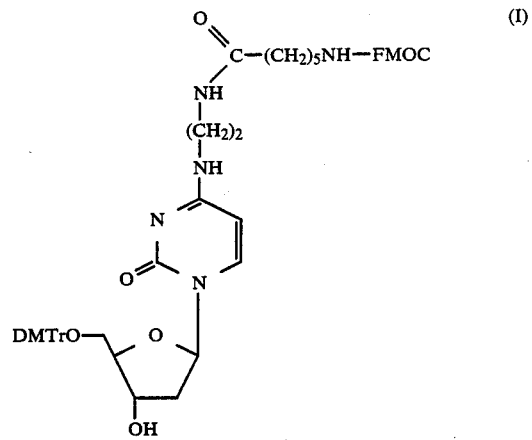

A solution of tetrabutylammonium fluoride (15 mmole, 15 ml of a 1M solution in THF) and aqueous HF (1.05 ml of a 50% aqueous solution) were mixed and dried by coevaporation of pyridine. The residue was dissolved in pyridine (15 ml) and added to G (7.2 g, 7.3 mmole) which was dissolved by sonication. After 18 hours at 4° C. the reaction mixture was diluted with 200 ml methylene chloride. Concentrated aqueous NaHCO$_3$ was carefully added followed by solid NaHCO$_3$, added gradually so as to neutralize the HF/pyridine. After drying over Na$_2$SO$_4$, the organic phase was concentrated to an oil, which was subjected to silica gel chromatography. The product N$^4$-(N-FMOC-6-aminocaproyl-2-aminoethyl)-5'-dimethoxytri-tyl-2'-deoxycytidine (I) was eluted with 5-6% methanol in methylene chloride to give an 86% yield (6.0 g).

EXAMPLE 9

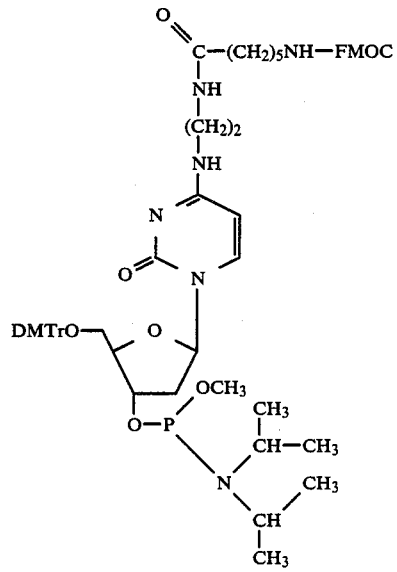

To 5.1 g (5.7 mmole) of I in methylene chloride containing (diisopropylethylamine) was added

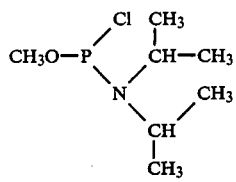

(chloro-N,N-diisopropylaminomethoxy phosphine, 1.3 ml [1.2 eq.], K) at 0° C. under argon. After 1 hr, ethyl acetate (200 ml) was added and washed with 80% saturated aqueous sodium chloride; after drying of the organic phase over $Na_2SO_4$, the product in methylene chloride was added dropwise to hexane at −40° C. to precipitate 4.43 g (75%) of J.

EXAMPLE 10
Probe Preparation (Fluorescein Label)

Synthetic oligonucleotides were prepared by an automated phosphoramidite method as described in Warner et al., *DNA* 3:401 (1984). Purification was carried out according to Sanchez-Pescador and Urdea, *DNA* 3:339 (1984).

The aminoethyl derivative of deoxycytidine as prepared in Example 2 was incorporated by standard coupling procedures during the oligonucleotide synthesis and the purified modified oligonucleotides were used for incorporation of a fluorescein label as follows. To a dried sample (3–5 OD 260 units) of the aminoethyl deoxycytidine containing oligomer were added 50 μl of DMF and 25 μl of the 0.2M stock solution of A described above. After 18 h at room temperature, the solution was partially purified by Sephadex G-10 chromatography eluted with water, dried and further purified by polyacrylamide gel, as above.

EXAMPLE 11
Probe Preparation (Biotin Label)

Using the probes containing aminoethylcytidine as prepared in the previous example, biotin labeling was achieved as follows. The oligonucleotide (3–5 OD 260 units) was taken up in 50 μl 0.1M sodium phosphate, pH 7.0 and 50 μl of DMF to which 100 μl of a DMF solution containing 1 mg of a "long chain" N-hydroxysuccinimidyl biotin (Pierce Chemical) was added. After 18 h at room temperature, the biotinylated probe was purified as described for the fluorescein labeled probe.

EXAMPLE 12
Synthesis of Horseradish Peroxidase (HRP): DNA Conjugates

Sequence 1 (5'-[LCA]CTGAACGTTCAAC-CAGTTCA-3') where LCA=$N^4$(6-aminocaproyl-2-aminoethyl)-deoxy cytidine) was synthesized chemically and purified as described elsewhere (Warner, et al. (1984) *DNA* 3, 401). To 10 OD 260 units dissolved in 50 μl of water were added 10 μl of 1.0 M sodium borate, pH 9.3, and 500 μl of distilled dimethylformamide containing 20 mg of p-phenylene diisothiocyanate. The solution was vortexed and set for 2 hr at room temperature in the dark. Approximately 3 ml of n-butanol was then added. After vortexing, adding 3 ml of water, and vortexing again, the tube was centrifuged and the yellowish upper layer discarded. The extraction process was repeated with subsequent n-butanol additions until an final volume of approximately 50 μl was obtained.

The butanol was removed by evacuation, then 10 mg of HRP in 200 μl of 0.1 M burate, pH 9.3, was added. The mixture was vortexed, then set at room temperature overnight in the dark.

Separation of the HRP-DNA conjugate from free enzyme and DNA was achieved on a 7% polyacrylamide gel. The 250 μl reaction mixture was quenched with 100 μl of 25% glycerol, 0.5% SDS, 0.5% bromophenol blue, 2.5 mM EDTA. The solution was then distributed into 10 lanes of a 20×20 0.15 cm gel and run at 60 mAmps under standard conditions (Maxam, A., and Gilbert, W., (1980) *Methods in Enzymol* 65, 499–560) until the bromophenol blue was about ⅔ down the gel. The gels were set on Baker F-254 silica 60 plates that had been covered with Saran Wrap (Dow) and examined with a handheld UV-short wavelength lamp held above. Pictures of the UV-shadowed bands were taken with a Polaroid MP-4 camera system fitted with a Kodak No. 59 green filter, after which the bands were cut out with a razor blade. The bands were put into a 10-ml Bio-Rad polypropylene econo-columns to which 3 ml of 0.1 M sodium phosphate, pH 7.5, was added, then set at room temperature overnight.

The contents of the column were filtered through the frit at the column bottom into an Amicon centricon microconcentrator that had been washed twice with distilled water. The HRP-DNA conjugate was then concentrated by centrifugation at 3500 rpm and washed twice with 1× PBS also by centrifugation. The final solution was then stored at 4° C.

EXAMPLE 13
Assay for HBV DNA Using HRP-DNA Probe and a Biotinylated Probe Bound to an Avidin Bead Biotin labeled probe (B'; 1000 pmoles in 66.7 μl of water) was combined with 5 ml of a 0.25% (w/v) solution of 0.8 μ avidin beads (Pandex laboratories), 1 ml of 20× SSC, 0.5 ml of 1% NP40 and 0.6 of 1 mg/ml polyA. After 1 h at 37° C., the beads were washed twice by centrifugation with 4× SSC, 0.1% NP40 then stored in 2.5 ml of this solution. The HBV analyte (described in copending application Ser. No. 807,624, previously incorporated by reference) in 3 μl water was diluted into 10 μl of 4× SSC, 1% SDS, 0.5 M NaOH and 1.5 pmoles of the labeling and capturing probe sets. The mixture was heated to 95° C. for 10 min., cooled on ice and neutralized with 5 μl of 1 M acetic acid, then 10 μl of the biotin probe beads were added and the solution was incubated at 37° C. for 1 h.

The beads were washed twice by centrifugation with 4× SSC, 0.1% NP40, then taken up in 50 μl of 0.1% NP40, 1 mg/ml polyA, 10 mg/ml BSA, 1× PBS containing 1 pmole of HRP-DNA conjugate and set a 37° C. for 1 h. The beads were washed with 0.1% NP40, 1× PBS three times then transferred in 50 μl to a microtiter dish. To each well, 50 μl of fresh OPD solution (98 mg OPD (O-phenylenediamine), 20 μl of 30% $H_2O_2$ in 10 ml of 50 mM sodium citrate pH 5.0) was added, mixed and set 5 min. at 37° C. The absorbances were recorded on a microtiter plate reader. Control hybridizations contained no HBV analyte.

TABLE 4

| Condition | Absorbance Reading |
| --- | --- |
| 1 pmole | >2 |
| 0.1 pmole | >2 |
| 0.01 pmole | 0.88 ± 0.23 |
| 1 fmole | 0.20 ± 0.05 |

TABLE 4-continued

| Condition | Absorbance Reading |
| --- | --- |
| 0.1 fmole | 0.07 ± 0.03 |
| NO ANALYTE | 0.01 ± 0.01 |

We claim:

1. A method of making a polynucleotide probe, comprising:
   (a) providing a modified nucleotide given by the structure

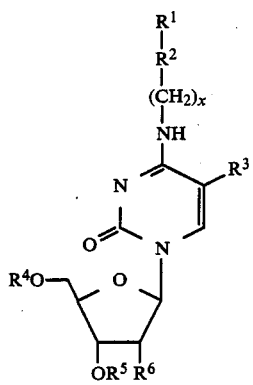

wherein:
   $R^1$ is a protected or unprotected —$NH_2$, —COOH or —SH group;
   $R^2$ is a bond or an amide, thioether or disulfide linking moeity;
   $R^3$ is hydrogen, methyl, bromine, fluorine or iodine;
   $R^4$ is selected from the group consisting of hydrogen, acid-sensitive, base-stable blocking groups and acyl capping groups;
   $R^5$ is a phosphorus derivative selected from the group consisting of $PO_3H_2$, phosphotriesters, phosphodiesters, phosphites, phosphoramidites, H-phosphonates and phosphorothioates and may be bound through $R^5$ to a solid support;
   $R^6$ is H, OH, or OR where R is an acid-sensitive, base-stable protecting group; and
   x is an integer in the range of 1 and 8 inclusive; and
   (b) sequentially adding nucleotides to either the 3' and of said modified nucleotde, the 5' end, or both, wherein a fraction of the added nucleotides comprise a plurality of said modified nucleotides, thereby providing a polynucleotide probe having said modified nucleotides incorporated at predetermined, spaced apart positions.

2. The method of claim 1, further including, after (b):
   (c) labeling the modified nucleotides within said polynucleotide probe by derivatization with a labeling species at the $R^1$ moiety.

3. The method of claim 1, further including, prior to step (a), labeling each of said modified nucleotides to be incorporated into said probe by derivatization with a labeling species at the $R^1$ moiety.

4. The method of claim 1, wherein $R^1$ is a protected or unprotected —$NH_2$ group.

5. The method of claim 4, wherein $R^2$ is a bond or an amide linking moiety.

6. The method of claim 5, wherein $R^4$ and $R^6$ are hydrogen.

* * * * *